United States Patent
Gillam et al.

(10) Patent No.: US 8,438,182 B2
(45) Date of Patent: May 7, 2013

(54) PATIENT IDENTIFICATION

(75) Inventors: Michael T. Gillam, Washington, DC (US); Jonathan A. Handler, Chicago, IL (US); Craig Feied, Kirkland, WA (US); John C. Gillotte, Washington, DC (US)

(73) Assignee: Microsoft Corporation, Redmond, WA (US)

( * ) Notice: Subject to any disclaimer, the term of this patent is extended or adjusted under 35 U.S.C. 154(b) by 0 days.

(21) Appl. No.: 12/981,549

(22) Filed: Dec. 30, 2010

(65) Prior Publication Data

US 2012/0173576 A1 Jul. 5, 2012

(51) Int. Cl.
*G06F 7/00* (2006.01)
*G06F 17/30* (2006.01)

(52) U.S. Cl.
USPC ............ 707/780; 707/781; 707/825; 705/2; 705/3

(58) Field of Classification Search .................. 705/2–3
See application file for complete search history.

(56) References Cited

U.S. PATENT DOCUMENTS

| | | | |
|---|---|---|---|
| 6,498,861 B1* | 12/2002 | Hamid et al. | 382/124 |
| 7,092,553 B2* | 8/2006 | Kuepper et al. | 382/116 |
| 2002/0101619 A1 | 8/2002 | Tsubaki et al. | |
| 2004/0122705 A1* | 6/2004 | Sabol et al. | 705/2 |
| 2005/0223016 A1* | 10/2005 | Wang et al. | 707/100 |
| 2006/0074280 A1 | 4/2006 | Martis et al. | |
| 2006/0074986 A1* | 4/2006 | Mallalieu et al. | 707/104.1 |
| 2006/0095429 A1* | 5/2006 | Abhyankar et al. | 707/7 |
| 2006/0293925 A1* | 12/2006 | Flom | 705/3 |
| 2007/0168232 A1* | 7/2007 | Kimmel | 705/2 |
| 2007/0172155 A1* | 7/2007 | Guckenberger | 382/305 |
| 2007/0241861 A1* | 10/2007 | Venkatanna et al. | 340/5.52 |
| 2007/0258626 A1* | 11/2007 | Reiner | 382/115 |
| 2007/0260492 A1* | 11/2007 | Feied et al. | 705/3 |
| 2008/0033919 A1* | 2/2008 | Arrouye et al. | 707/3 |
| 2008/0052312 A1* | 2/2008 | Tang et al. | 707/104.1 |
| 2008/0095410 A1* | 4/2008 | Shalev et al. | 382/115 |
| 2008/0120707 A1* | 5/2008 | Ramia | 726/5 |
| 2008/0235515 A1* | 9/2008 | Yedidia et al. | 713/186 |
| 2008/0313726 A1* | 12/2008 | Gardner | 726/9 |
| 2008/0317292 A1* | 12/2008 | Baker et al. | 382/115 |
| 2009/0003663 A1* | 1/2009 | Webster | 382/119 |
| 2010/0027852 A1* | 2/2010 | Hsieh et al. | 382/115 |
| 2010/0060411 A1* | 3/2010 | Ikegami | 340/5.53 |
| 2010/0228563 A1* | 9/2010 | Walker et al. | 705/2 |
| 2011/0106734 A1* | 5/2011 | Boult et al. | 706/12 |
| 2011/0130635 A1* | 6/2011 | Ross | 600/301 |
| 2011/0182480 A1* | 7/2011 | Murakami et al. | 382/115 |
| 2011/0221567 A1* | 9/2011 | Lehnert et al. | 340/5.82 |

OTHER PUBLICATIONS

Jain et al., An Introduction to Biometric Recognition, Jan. 2004, IEEE, vol. 14, No. 1, pp. 4-20.*
Byers, Jeff., "Mr. Patient, May I See Your ID?", Retrieved at <<http://www.cmio.net/index.php?option=com_articles&view=article&id=21827:mr-patient-may-i-see-your-id>>, Apr. 21, 2010, pp. 3.

(Continued)

*Primary Examiner* — Wilson Lee
*Assistant Examiner* — Jessica N Le

(57) ABSTRACT

The described implementations relate to patient identification. One implementation can acquire binary biometric data and structured data from a patient. This implementation can compare the acquired patient binary biometric data and structured data to binary biometric data and structured data associated with patient files in an electronic master patient index.

14 Claims, 4 Drawing Sheets

OTHER PUBLICATIONS

"Increasing Accuracy In Healthcare With ID Card Systems", Retrieved at http://www.fieldtechnologiesonline.com/article.mvc/Increasing-Accuracy-In-Healthcare-With-ID-Car-0001?VNETCOOKIE=NO>>, Mar. 1, 1998, pp. 2.

"Information security & privacy", Retrieved at <<http://www.security.harvard.edu/glossary-terms>>, Retrieved Date: Oct. 11, 2010, pp. 3.

Mancilla, et al., "Exploring Medical Identity Theft", Retrieved at <<http://perspectives.ahima.org/index.php?option=com_content&view=article&id=163&Itemid=56>>, Perspect Health Inf Manag, Sep. 16, 2009, pp. 10.

"Mount sinai medical center personal health card", Retrieved at <<http://www.smartcardalliance.org/resources/lib/Mount_Sinai_Profile.pdf>>, pp. 3, 2007.

* cited by examiner

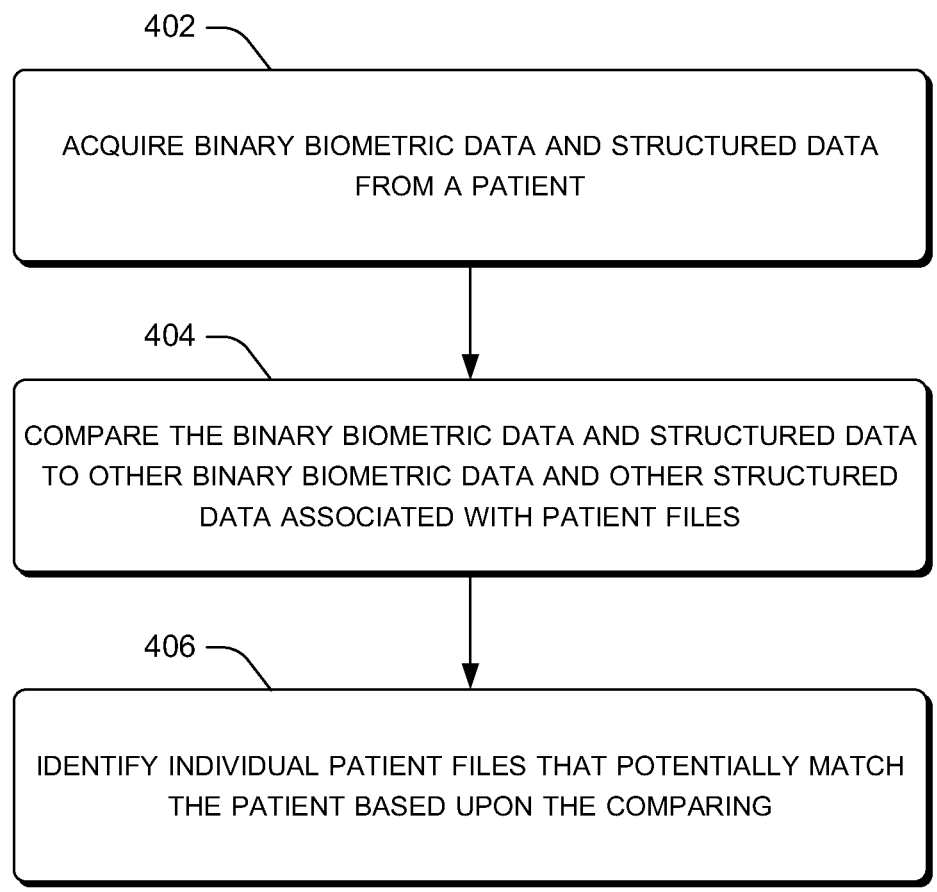

PATIENT IDENTIFICATION

BACKGROUND

Presently when a person or patient interacts with the health care system, textual or structured data, such as social security number, date of birth, gender, etc., is obtained from the person. The obtained structured data is compared to structured data in existing patient files in an attempt to match the patient to a file. One challenge is that in cases where the data are wrong, or missing, the algorithms begin to fail. For instance, sometimes patients are unconscious and don't have identification with them. In another example, patients that do not have insurance coverage sometimes provide contrived data or data from other individuals that have insurance coverage. In either case, not being able to match the patient with the proper file can compromise patient care.

SUMMARY

The described implementations relate to patient identification. One implementation can acquire binary biometric data and structured data from a patient. This implementation can compare the acquired patient binary biometric data and structured data to binary biometric data and structured data associated with patient files in an electronic master patient index.

Another implementation can acquire binary biometric data and structured data from a patient. This implementation can compare the binary biometric data and structured data to other binary biometric data and other structured data associated with patient files. This implementation can also identify individual patient files that potentially match the patient based upon the comparing.

One implementation can acquire binary biometric data and structured data from a patient and can access a set of patient files. This implementation can process the patient's binary biometric data utilizing a machine learning algorithm. This implementation can also attempt to determine that the patient cannot match an individual patient file by comparing the patient's processed binary data and the patient's structured data to contents of the individual patient file.

The above listed examples are intended to provide a quick reference to aid the reader and are not intended to define the scope of the concepts described herein.

BRIEF DESCRIPTION OF THE DRAWINGS

The accompanying drawings illustrate implementations of the concepts conveyed in the present application. Features of the illustrated implementations can be more readily understood by reference to the following description taken in conjunction with the accompanying drawings. Like reference numbers in the various drawings are used wherever feasible to indicate like elements. Further, the left-most numeral of each reference number conveys the Figure and associated discussion where the reference number is first introduced.

FIGS. 3-4 illustrate examples of flowcharts of patient identification methods in accordance with some implementations of the present concepts.

DETAILED DESCRIPTION

Overview

Figure 1:
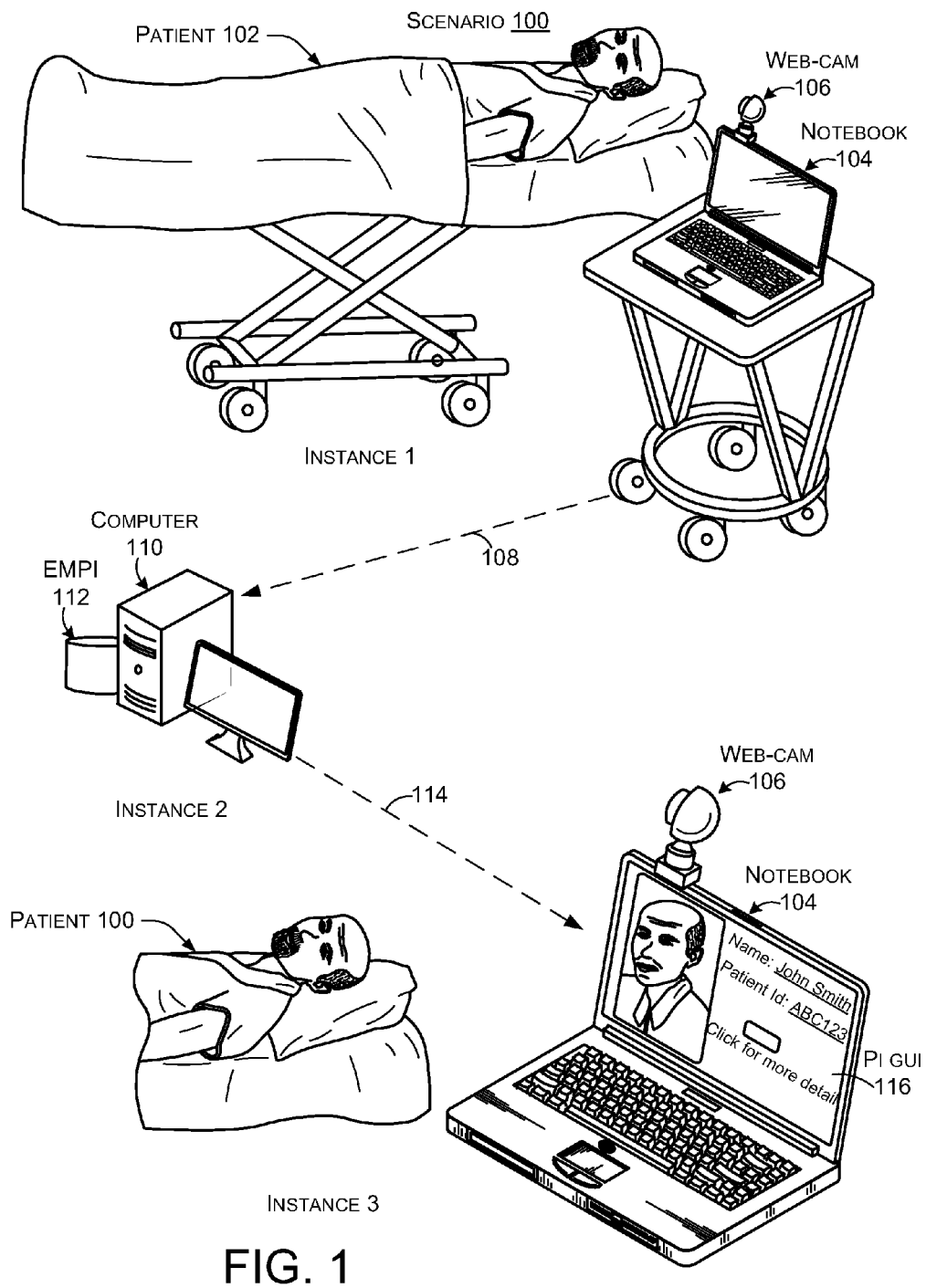
FIG. 1 shows an example of a scenario in which the patient identification concepts can be employed in accordance with some implementations of the present concepts.

This patent relates to patient identification. Currently, databases of patient files exist. Some of these databases are referred to as electronic master patient indexes (EMPIs). An EMPI can associate an individual patient file with a unique identifier or patient identifier, such as a name or a number. The present implementations can utilize biometric binary data obtained from the patient to determine whether a patient potentially matches or does not match a unique identifier (e.g., is this patient the same one as indicated by the unique identifier).

Biometric binary data can be any type of patient data that is not structured data. For instance, biometric binary data can be a photograph of the patient, or other image data from the patient, such as x-rays, CT scans, MRIs, electrocardiograms, etc. The biometric binary data, along with any structured data available from the patient can be compared to biometric binary data and/or structured data associated with patient files in the EMPI to automatically determine the patient's identity and/or to eliminate erroneous matches. An erroneous match is an instance where the results indicate that the patient is the same person as a patient in the EMPI when in fact they are different people.

Scenario Example

The discussion above broadly introduces patient identification concepts utilizing biometric binary data. To aid the reader in understanding these concepts, scenario 100 provides a tangible example to which the concepts can be applied. Scenario 100 involves instances 1-3, each of which is discussed below. Starting at instance 1, example scenario 100 involves a patient 102 that presents for care, such as in an emergency room. Assume for purposes of explanation that the patient is unconscious. Further, the only identification that the patient has is a debit card with the name "John Smith". Admissions staff can enter the name John Smith as structured data on an admissions graphical user interface generated on notebook computer 104. (The admissions graphical user interface is not shown in scenario 1 due to space constraints on the drawing page. A subsequent graphical user interface is shown relative to instance 3).

Binary biometric data can also be obtained from the patient 102. For instance, a web-cam 106 or other camera can capture binary biometric data in the form of a picture or image. The web-cam 106 can communicate the image to the notebook computer 104. Note that, as in this example, binary biometric data can be obtained specifically for the purposes of patient identification. Alternatively or additionally, binary biometric data may be obtained for clinical reasons and also used for patient identification. For example, protocols may indicate that an EKG should be obtained from an unconscious patient to ascertain heart function. The EKG can also be utilized for patient identification. The structured data in the form of patient name, John Smith and binary biometric data in the form of the patient image can be sent for processing as indicated by arrow 108.

In instance 2, computer 110 can perform processing on the received structured data and the binary biometric data of arrow 108 to determine if patient 102 already exists in the health care system. For instance, the computer 110 can automatically compare the acquired patient binary biometric data and structured data to binary biometric data and/or structured data associated with patient files in an electronic master patient index (EMPI) 112. This process is described in more detail below relative to FIG. 2, but briefly various machine learning algorithms can be applied to the patient's binary biometric data. The same machine learning algorithms can also be applied to binary biometric data in individual patient files.

The machine learning algorithms can output parameters from the patient's image data that, along with the patient's structured data, allows a more determinative comparison to the patient files than is otherwise possible. The comparison can produce a relatively highly accurate match between patient 102 and an individual patient file and/or reduce the likelihood of an erroneous match. Computer 110 can then format the results of the comparison and send the formatted results back to notebook computer 104 as indicated by arrow 114.

At instance 3, the formatted results received via arrow 114 can be utilized to generate a patient information graphical user interface (PI GUI) 116 on notebook computer 104. In this example, the patient information graphical user interface confirms that the patient is in fact named John Smith. The patient's unique identifier or patient identifier (Patient Id) is listed as ABC123. The user can also click to receive detailed information from the patient's file.

To summarize, this implementation can obtain binary biometric data from a patient and utilize the binary biometric data as well as any available structured data to correctly associate the patient with a patient identifier and can reduce or avoid erroneous associations.

System Example

Figure 2:
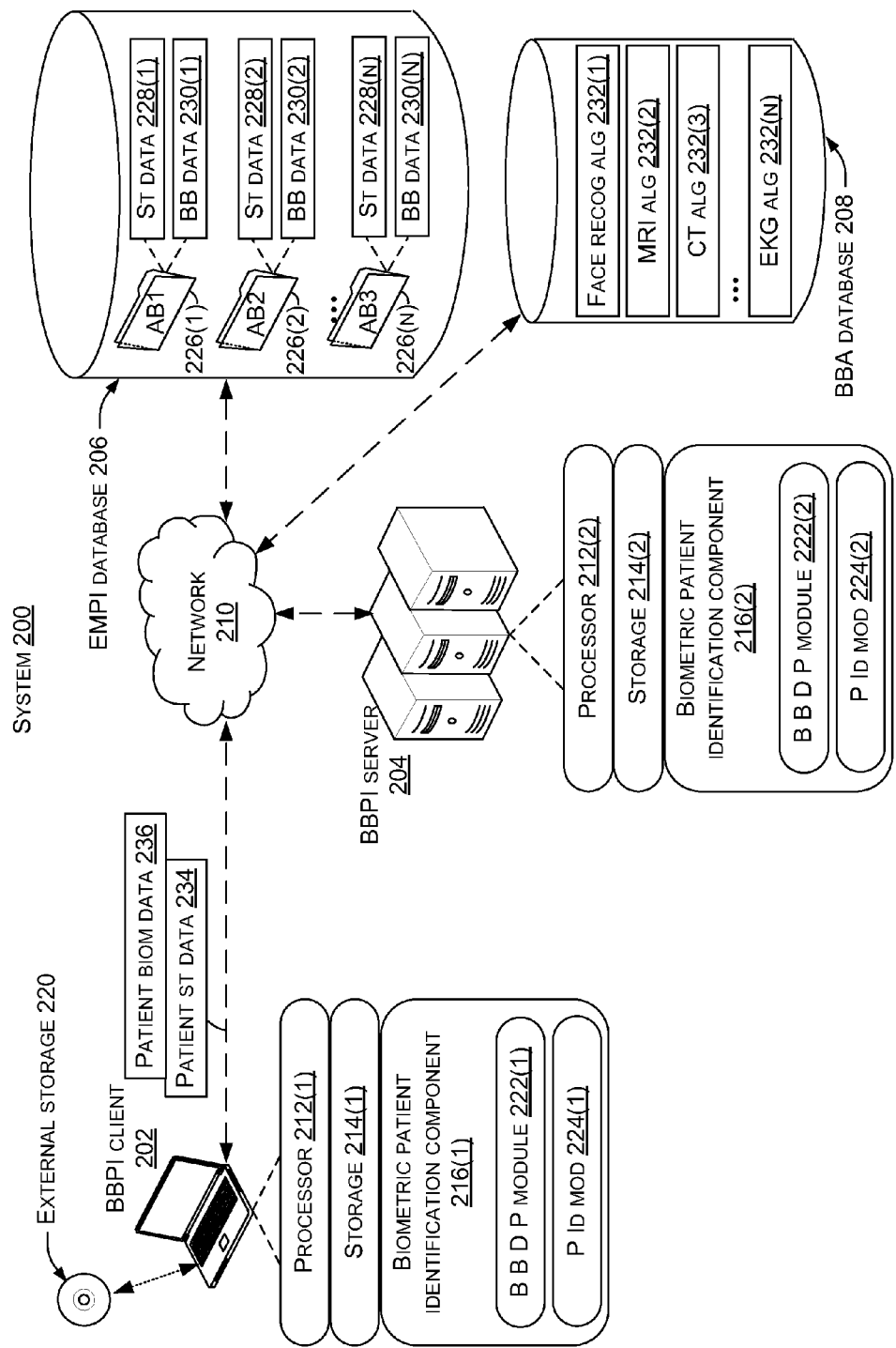
FIG. 2 shows an example of a patient identification system in accordance with some implementations of the present concepts.

FIG. 2 shows an example of a biometric binary patient identification system (BBPI system) 200. Example system 200 can include one or more biometric binary patient identification client computing device(s) (BBPI client) 202 and one or more biometric binary patient identification server computing device(s) (BBPI server) 204. BBPI system 200 can also include various resources. In this case, the resources are manifest as an electronic master patient index database 206 and a binary biometric algorithm database 208. The BBPI client 202, BBPI server 204, electronic master patient index (EMPI) database 206, and binary biometric algorithm (BBA) database 208 can communicate over one or more networks 210, such as, but not limited to, the Internet.

The term "computer" or "computing device" as used herein can mean any type of device that has some amount of processing capability. Examples of computing devices can include traditional computing devices, such as personal computers, cell phones, smart phones, personal digital assistants, or any of a myriad of ever-evolving or yet to be developed types of computing devices. Further, a BBPI system can be manifest on a single computing device or distributed over multiple computing devices.

In this case, BBPI client 202 and BBPI server 204 can each include a processor 212, storage 214, and a BBPI component 216. (A suffix '(1)' is utilized to indicate an occurrence of elements on BBPI client 202 and a suffix '(2)' is utilized to indicate an occurrence on the BBPI server 204. Generic references to these elements do not include a suffix.)

Processor 212 can execute data in the form of computer-readable instructions to provide a functionality. Data, such as computer-readable instructions, can be stored on storage 214. The storage can include any one or more of volatile or non-volatile memory, hard drives, and/or optical storage devices (e.g., CDs, DVDs etc.), among others. The BBPI client 202 and BBPI server 204 can also be configured to receive and/or generate data in the form of computer-readable instructions from an external storage 220.

Examples of external storage 220 can include optical storage devices (e.g., CDs, DVDs etc.), hard drives, and flash storage devices (e.g., memory sticks or memory cards), among others. In some cases, BBPI component 216(1) can be installed on the BBPI client 202 during assembly or at least prior to delivery to the consumer. In other scenarios, BBPI component 216 can be installed by the consumer, such as a download available over network 210 and/or from external storage 220. Similarly, BBPI server 204 can be shipped with BBPI component 216. Alternatively, the BBPI component 216 can be added subsequently from network 210 or external storage 220. The BBPI component 216 can be manifest as a freestanding application or as an application part, among other examples. In various implementations, BBPI component 216 can be implemented as software, hardware, and/or firmware, or in another manner.

In the present implementation, the BBPI component 216 can include a binary biometric data processing module (BBDP) 222 and a patient identification module (P Id module) 224. The BBPI component 216 can achieve the functionality described above relative to FIG. 1. Further detail is offered here relative to how the BBDP module 222 and the P Id module 224 contribute to the functionality of the BBPI component 216.

The electronic master patient index (EMPI) database 206 can include and/or reference patient files 226(1)-226(N). Each patient file can be associated with a unique identifier or patient identifier. In this example, patient file 226(1) is associated with unique identifier AB1, patient file 226(2) is associated with unique identifier AB2, and patient file 226(3) is associated with unique identifier AB3. Each patient file 226(1)-226(N) can include and/or reference structured data 228 and in some cases binary biometric data 230.

The binary biometric algorithm (BBA) database 208 can contain various binary biometric algorithms 232 that can be utilized to derive identification parameters from binary biometric data and/or otherwise process the binary biometric data. In the illustrated example the BBA database 208 contains a face recognition algorithm 232(1), an MRI algorithm 232(2), a CT algorithm 232(3), and an EKG algorithm 232(N). Algorithms can be added, deleted and/or updated in the BBA database 208. Further, the database can contain multiple algorithms of a single type. For instance, the BBA database could include additional face recognition algorithms beyond the illustrated face recognition algorithm 232(1).

The BBDP module 222 can be configured to compare binary biometric data and structured data obtained from a patient (such as via BBPI client 202) to binary biometric data and/or structured data contained in patient files 226. For instance, assume that BBPI client 202 is functioning as an intake computer for a new patient. Patient structured data 234 and patient biometric data 236 can be generated at the BBPI client 202 and sent to the BBPI server 204. The BBDP module 222 can obtain the patient structured data 234 and patient biometric data 236.

In one configuration, the BBDP module 222 can process the patient biometric data 236 with one or more of the binary biometric algorithms 232 to derive identification parameters. The identification parameters can be useful in matching the patient to an individual file 226(1)-226(N) and/or can be useful in determining that the patient cannot match an individual file. The BBDP module can access individual files 226(1)-226(N) and can process the patient biometric data 236 with one or more of the binary biometric algorithms 232 to derive identification parameters. The binary biometric algorithms 232 applied to the binary biometric data in the files may or may not be the same algorithms applied to the patient biometric data 236. For instance, assume for purposes of explanation that the patient biometric data 236 is a picture of the torso and head of the patient and that an individual file 226(1) contains an MRI image of a patient's torso. The BBDP module may apply the facial recognition algorithm 232(1) to the patient biometric data 236 to derive identification parameters and the MRI algorithm 232(2) to the binary biometric data 230(1) to derive identification parameters. Some or all of these identification parameters may prove useful in comparing the patient and the file.

In some cases, the BBDP module 222 may process the binary biometric data 230(1)-230(N) in real-time when the patient biometric data 236 is received. Stated another way, the patient biometric data 236 can be processed at generally the same time as the binary biometric data 230(1)-230(N), such as within +/−one second. In other implementations, the BBDP module may cause the binary biometric algorithms 232 to operate on the binary biometric data 230(1)-230(N) in advance. For instance, the BBDP module may process binary biometric data 230(1)-230(N) when resources are available, such as in the late night or early morning hours. The BBDP module can store the resulting identification parameters, such as in the respective patient files 226(1)-226(N). In some cases, the BBDP module can treat the identification parameters as metadata that is tagged to the binary biometric data.

In the pre-processing scenario, when patient structured data 234 and patient biometric data 236 are received, the BBDP module 222 can process the patient biometric data 236 to derive identification parameters which can then be compared to the identification parameters stored in the patient files 226(1)-226(N). This later (pre-processing) configuration may provide faster results than the former configuration, especially in instances where a patient presents during high resource utilization times. In either scenario, the identification parameters from the processed patient biometric data 236 and the identification parameters from the processed binary biometric data 230(1)-230(N) can be available to the P Id module 224.

The P Id module 224 can be configured to communicate with the BBDP module 222. The P Id module can analyze the identification parameters from the processed patient biometric data 236 and the identification parameters from the processed binary biometric data 230(1)-230(N) as well as the patient's structured data 234 and structured data 228(1)-228(N).

In some implementations, the P Id module 224 may compare most or all of the identification parameters and the structured data from the patient to identification parameters and structured data form a patient file to generate a cumulative similarity score between the patient and the file. The similarity scores can be stored in a similarity index that is maintained by the P Id module. Some of these implementations may assign equal weights to the various identification parameters. For instance, hair color may be an identification parameter that is given a low weight since hair color is often changed. In contrast, another identification parameter such as inter-pupil distance may be given a relatively higher weight since it is unchanging. Still other implementations may emphasize individual identification parameters that are especially indicative of whether the patient matches or cannot match the file. For instance, assume that an identification parameter derived from a CT scan of the patient indicates that the patient has two kidneys. Further assume that the processing of a CT scan in an individual file indicates that the person associated with that file only has one kidney. Given that the image in the file is older than the image that was just taken from the patient, the patient cannot be the person associated with that file.

While the above implementations compare individual identification parameters that are readily understood by a human, the P Id may employ machining learning algorithms that can determine that the patient cannot match a file based upon parameters that are not readily understood by a human and/or are beyond the scope of this document. For instance, the P Id module may leverage CT processing algorithm(s). The CT processing algorithm(s) may determine based upon a multitude of parameters that a CT scan from the patient is unlikely to be, or cannot be, from the same person as a CT scan in an individual file.

BBPI component 216 can also used to reconcile archives of older data. For instance, the BBPI component can merge two or more hospital systems into a single system. Further, the BBPI component can offer a quality control function in that this merge could be done automatically. However, the merge function can be based upon a confidence threshold. The BBPI component can automatically merge files that satisfy the threshold (e.g., relatively high confidence of a match). In contrast, the BBPI component may not merge files that do not satisfy the threshold. For instance, the BBPI component could create a list of patients and/or files to be reviewed by specialists for final determination.

Such a threshold could also be applied in patient identification scenarios. For instance, when a new patient enters the system, the BBPI component 216 could present a list of potential matches with their relative likelihoods (e.g., confidence score). In such a scenario the caregivers could evaluate the list and make a final determination.

In summary, the P Id module 224 can utilize the patient structured data 234 and patient biometric data 236 to identify individual files 226(1)-226(N) that are more likely to match the patient from those files that are less likely to match the patient. In some implementations, the P Id module can exclude individual files as potential matches and thereby reduce erroneous matching. Some implementations can rank the remaining files and cause one or more relatively high ranking files to be sent back to the BBPI client 202 for further consideration by admissions staff. Stated another way, the patient can be compared to a set of files. A subset of non matching files can be excluded from further consideration so that resources can be allocated to analyzing the remaining files.

In system 200, both the BBPI client 202 and the BBPI server 204 are illustrated with full feature BPI components 216. However, other implementations may utilize other configurations with little or no processing performed at the client and/or configurations where the processing is distributed over multiple distributed computers and/or the processing is performed in the cloud. In other configurations, the role of the BBPI server 204 could be reduced or eliminated such that the BBPI client 202 interacts directly with the EMPI database 206 and the BBA database 208 and performs the associated processing locally. In still other implementations, the electronic master patient index database 206 and binary biometric algorithm database 208 can be manifested on the BBPI server 204.

Method Examples

Figure 3:
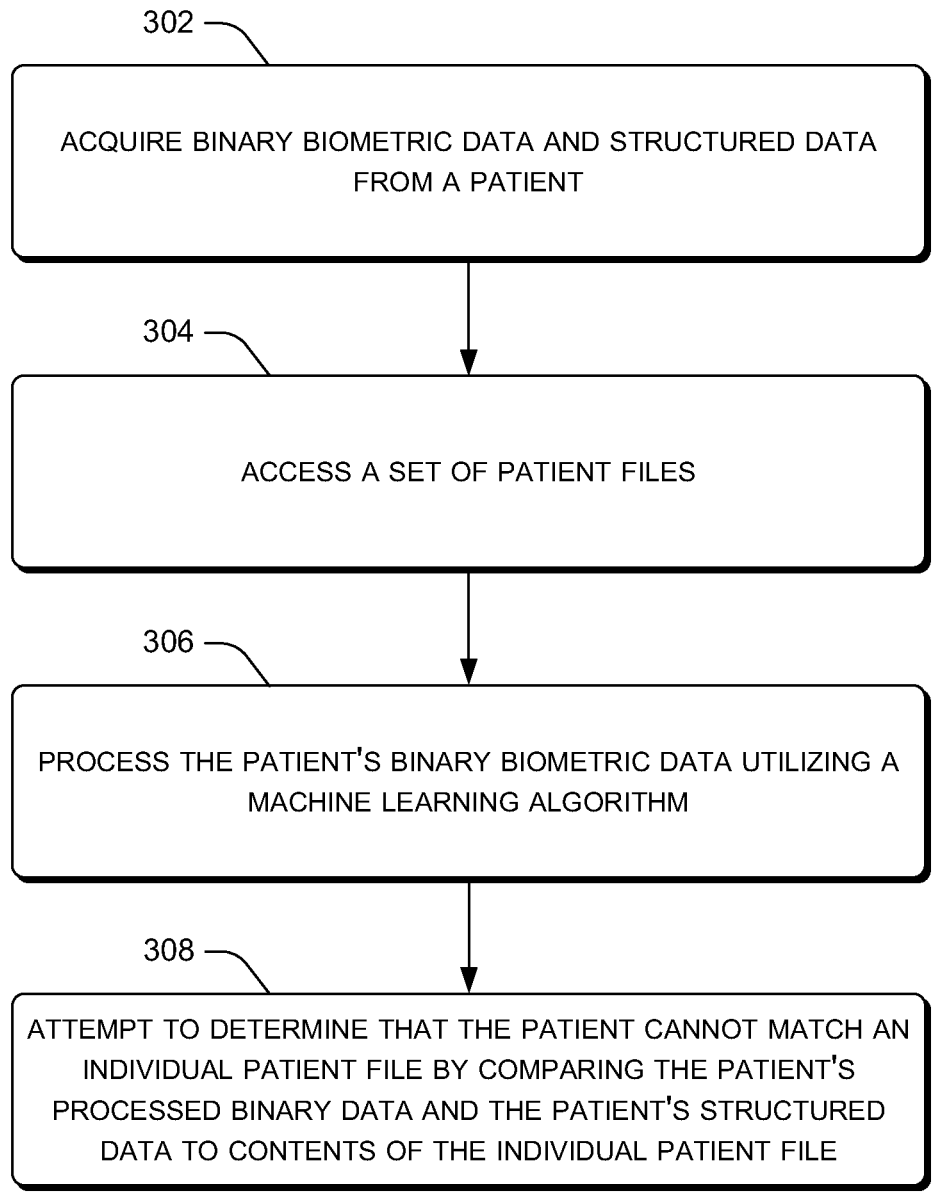

FIG. 3 illustrates a flowchart of a patient identification technique or method 300.

At block 302, the method can acquire binary biometric data and structured data from a patient. Examples are described above relative to FIGS. 1-2.

At block 304, the method can access a set of patient files. In some implementations, this set of patient files may be manifest as an EMPI that refers to each patient file with a unique identifier or patient identifier. An example of an EMPI is described above relative to FIG. 2.

At block 306, the method can process the patient's binary biometric data utilizing a machine learning algorithm. The term "machine learning" is generally used to refer to various types of techniques, including, but not limited to, artificial intelligence (e.g., genetic algorithms), machine learning, stochastic, probabilistic, and/or Bayesian techniques.

At block 308, the method can attempt to determine that the patient cannot match an individual patient file by comparing the patient's processed binary data and the patient's structured data to contents of the individual patient file. In some cases, a single identification parameter from the patient's binary biometric data may be irreconcilable with the occurrence of the identification parameter in the patient file. In other cases, the patient's binary biometric data and structured data when compared as a whole may be irreconcilable with the binary biometric data and/or structured data of the file. Specific examples of these two scenarios are described above.

FIG. 4 illustrates a flowchart of another patient identification technique or method 400.

At block 402, the method can acquire binary biometric data and structured data from a patient.

At block 404, the method can compare the binary biometric data and structured data to other binary biometric data and other structured data associated with patient files. Various machine learning algorithms can be employed to perform the comparing.

At block 406, the method can identify individual patient files that potentially match the patient based upon the comparing. The identification of potential matches can result from the machine learning algorithm. In other instances, the identification can be achieved via further processing of the output of the machine learning algorithm(s).

The order in which the example methods are described is not intended to be construed as a limitation, and any number of the described blocks or steps can be combined in any order to implement the methods, or alternate methods. Furthermore, the methods can be implemented in any suitable hardware, software, firmware, or combination thereof, such that a computing device can implement the method. In one case, the method is stored on one or more computer-readable storage media as a set of instructions such that execution by a computing device causes the computing device to perform the method.

CONCLUSION

Although techniques, methods, devices, systems, etc., pertaining to patient identification are described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A system comprising:
at least one computer-readable storage device having instructions stored thereon; and
a processor coupled to the computer-readable storage device to execute the instructions to accomplish a method comprising:
acquiring binary biometric data and structured data from a patient, wherein the binary biometric data include more than one type of binary biometric data;
processing the acquired binary biometric data utilizing multiple binary biometric machine learning algorithms to derive a first set of identification parameters;
processing other binary biometric data associated with a patient file stored in an electronic master patient index (EMPI) database to derive a second set of identification parameters, wherein the first set and the second set of identification parameters are derived from the same types of binary biometric data or different types of binary biometric data;
generating a cumulative similarity score comprising multiple different identification parameters between the first set and the second set of identification parameters, wherein each individual identification parameter in the first set and the second set of identification parameters are given equal weights or relative weights;
identifying whether the patient file matches the patient based upon the cumulative similarity score;
excluding patient files that are unlikely to match the patient based upon respective cumulative similarity scores; and
ranking remaining non-excluded files of the patient files.

2. The system of claim 1, wherein the acquiring comprises acquiring for clinical reasons.

3. The system of claim 1, wherein the multiple binary biometric machine learning algorithms are applied to the acquired binary biometric data and to the other binary biometric data at generally the same time or the multiple binary biometric machine learning algorithms are applied to the other binary biometric data before acquiring the binary biometric data from the patient.

4. The system of claim 1, wherein the identifying identifies an instance where the patient file in the electronic master patient index (EMPI) database does not match the patient.

5. The system of claim 1 further comprising: where one or more of the respective cumulative similarity scores satisfies a threshold, causing a patient identifier associated with one or more of the patient files to be presented on a graphical user interface as a potential match to the patient.

6. The system of claim 1, wherein the first set and the second set of identification parameters include multiple identification parameters, and wherein the multiple identification parameters equal or do not equal the multiple different identification parameters.

7. The system of claim 6, wherein the multiple identification parameters of the first set of identification parameters all equal the multiple identification parameters of the second set of identification parameters.

8. A method comprising:
acquiring binary biometric data and first structured data from a patient for clinical reasons, wherein the binary biometric data include more than one type of binary biometric data;
processing the acquired binary biometric data utilizing a machine learning algorithm to derive a first set of identification parameters;
accessing, by a computing processor, a set of patient files stored in an electronic master patient index (EMPI) database that includes a second set of identification parameters from other binary biometric data, and second structured data;
generating a cumulative similarity score comprising multiple different identification parameters between the first set and the second set of identification parameters and the first and second structured data, wherein each individual identification parameter of the first set and the second set of identification parameters are given equal weights or relative weights;

determining, by the computing processor, that the patient does not match an individual patient file upon comparing the cumulative similarity score of the multiple different identification parameters between the first set of identification parameters and the second set of identification parameters, wherein the first set of identification parameters and the second set of identification parameters are derived from the same types of binary biometric data or different types of binary biometric data;

excluding a subset of non-matching patient files from the set of patient files based upon the cumulative similarity score; and ranking remaining files of the set of patient files as potential matches with the patient utilizing a similarity index.

9. A system comprising:

a memory;

a processor coupled to the memory to execute at least one of:

a binary biometric data processing module configured to process binary biometric data and structured data obtained from a patient for clinical reasons utilizing at least a first binary biometric machine learning algorithm from a database of available binary biometric machine learning algorithms to derive a first set of identification parameters and further configured to obtain a second set of identification parameters from other binary biometric data and other structured data contained in patient files stored in an electronic master patient index (EMPI) database, wherein the second set of identification parameters are obtained with at least a second binary biometric machine learning algorithm from the database; and a patient identification module configured to:

communicate with the binary biometric data processing module, compare the first set of identification parameters and the second set of identification parameters to generate a cumulative similarity score comprising multiple different identification parameters between the patient and individual patient files, wherein contributions of the first set and the second set of identification parameters are given equal weights or relative weights, exclude the individual patient files that are unlikely to match the patient based upon the cumulative similarity score, and rank remaining non-excluded files of the patient files.

10. The system of claim 9, wherein the binary biometric data processing module and the patient identification module occur on a server computer.

11. The system of claim 9, wherein the electronic master patient index (EMPI) database that contains the patient files and associates one of the individual patient files with an unique identifier.

12. The system of claim 9, wherein the binary biometric data processing module and the patient identification module are manifested as software modules stored on a computer-readable storage device.

13. The system of claim 9, wherein the at least a first binary biometric machine learning algorithm comprises multiple binary biometric machine learning algorithms and the at least a second binary biometric machine learning algorithm comprises multiple different binary biometric machine learning algorithms.

14. The system of claim 9, wherein the at least a first binary biometric machine learning algorithm and the at least a second binary biometric machine learning algorithm are the same.

* * * * *